US00PP14437P39

(12) United States Plant Patent
Whetman

(10) Patent No.: US PP14,437 P3
(45) Date of Patent: Dec. 30, 2003

(54) DIANTHUS PLANT NAMED 'RED DWARF'

(50) Latin Name: *Dianthus×hybrida*
Varietal Denomination: Red Dwarf

(76) Inventor: John Whetman, Houndspool Ashcombe Road, Dawlish Devon (GB), EX7 0QP ( * ) Notice: Subject to any disclaimer, the term of this patent is extended or adjusted under 35 U.S.C. 154(b) by 0 days.

(21) Appl. No.: 10/071,113

(22) Filed: Feb. 7, 2002

(65) Prior Publication Data

US 2003/0150036 P1 Aug. 7, 2003

(51) Int. Cl.[7] ..... A01H 5/00
(52) U.S. Cl. ..... Plt./283

(58) Field of Search ..... Plt./283, 278, 273, Plt./272

(56) References Cited

PUBLICATIONS

The New Royal Horticultural Society Dictionary of Gardening, vol. 2, Editor–in–Chief Anthony Huxley, The Stockton Press, New York, 1992, pp 50–56.*

* cited by examiner

*Primary Examiner*—Anne Marie Grunberg

(57) ABSTRACT

A new cultivar of Dianthus named 'Red Dwarf' that is characterized by vigor, red flowers with a dark red center, a compact cushion habit and a long flowering season. In combination these traits set 'Red Dwarf' apart from all other existing varieties of Dianthus known to the inventor.

2 Drawing Sheets

Genus: Dianthus.
Species: ×hybrida.
Denomination: Red Dwarf.

CROSS-REFERENCES TO RELATED APPLICATIONS

The application for this new invention is co-pending with one other application entitled 'Neon Star'. 'Neon Star' is derived from the same breeding program having the same inventor and filing date as the present application entitled Dianthus 'Red Dwarf'.

BACKGROUND OF THE INVENTION

The present invention relates to a new and distinct dwarf variety of Carnation that is grown for its vigor, red flower with a darker red center, long flowering season and compact tight cushion habit. The new cultivar is known botanically as Dianthus×hybrida and will be referred to hereinafter by the cultivar name 'Red Dwarf'.

'Red Dwarf' is the product of a breeding program conducted by the inventor in a cultivated area of Houndspool, Dawlish, Devon, United Kingdom. The primary focus of the breeding program was to produce dwarf varieties exhibiting a wide range of flower colors, and perfume scented flowers with a long flowering season. The breeding program was established in 1969 in a cultivated area of Houndspool, Dawlish, Devon, United Kingdom. 'Red Dwarf' is one seedling that resulted from a large number of seedlings produced by Dianthus 'Brehemen' (unpatented).

'Red Dwarf' is a hybrid produced by induced hybridization and was selected by the inventor in 1996 for its vigor, red flower with darker red center, compact tight cushion habit and long flowering season. The male parent is an unidentified Dianthus and the female parent is the crimson flowered Dianthus 'Brehemen' (unpatented). 'Red Dwarf' is distinguishable from the female parent plant by its flower color, longer flowering season and more compact habit. The flower color of 'Brehemen' is N34A, whereas the flower of 'Red Dwarf' is red with a darker red center. The diameter of the 'Brehemen' flower is 1.5 cm. in diameter, whereas the flower of 'Red Dwarf' is 35 mm. in diameter. The length of flowering for 'Brehemen' is 5 weeks, whereas the length of flowering time for 'Red Dwarf' is 26 weeks. Individual flowers last approximately 10 days on 'Red Dwarf'.

In comparison, the plants most similar to 'Red Dwarf' are Dianthus 'Gipsy Star' (unpatented) and Dianthus 'Fusilier' (unpatented). 'Red Dwarf' differs from the comparison varieties in greater vigor, larger flowers and longer flowering season. 'Red Dwarf' is similar to 'Gypsy Star' in vigour but is 250% of the vigour of 'Fusilier'. The flower diameter of 'Gypsy Star' is 1.5 cm. and the individual flower duration 20 weeks. The flower diameter of 'Fusilier' is 1.0 cm. and the individual flower duration is 15 weeks.

Asexual reproduction of the new cultivar was first accomplished in 1996 by the inventor using softwood shoot cuttings in a cultivated area of Houndspool, Dawlish, Devon, United Kingdom. Since that time the characteristics of the new cultivar have been determined stable and are reproduced true to type in successive generations.

SUMMARY OF THE INVENTION

The following traits have been repeatedly observed and represent the characteristics of the new cultivar 'Red Dwarf'. These traits in combination distinguish this cultivar from all other commercial varieties known to the inventor. 'Red Dwarf' has not been tested under all possible conditions and phenotypic differences may be observed with variations in environmental, climatic and cultural conditions.

1. Dianthus 'Red Dwarf' exhibits a compact, tight cushion growth habit.

2. Dianthus 'Red Dwarf' exhibits scented red flowers with darker red centers.

3. Dianthus 'Red Dwarf' is vigorous.

4. Dianthus 'Red Dwarf' reaches 10–12 cm. in height including flower stalks and 20–25 cm. in width at maturity.

5. Dianthus 'Red Dwarf' exhibits a long flowering season of 26 weeks.

6. Dianthus 'Red Dwarf' is hardy to minus 15° Centigrade.

BRIEF DESCRIPTION OF THE DRAWINGS

The accompanying drawings illustrate the overall appearance of the new cultivar 'Red Dwarf'showing the colors as true as it is reasonably possible to obtain in colored reproduction of this type. Colors in the drawings may differ from the color values cited in the detailed botanical description, which more accurately describe the actual colors of the new variety 'Red Dwarf'.

The drawing on sheet 1 illustrates an entire mature plant.

The drawing on sheet 2 is a close-up view of the flower. Both drawings are photographs taken of plants in Houndspool, Dawlish, Devon, United Kingdom in October 2001. No chemicals were used in treating the illustrated plants. Both drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Red Dwarf'. Data was collected from mature plants in the Houndspool, Dawlish, Devon, United Kingdom. The color determinations are in accordance with the 2001 Royal Horticultural Color Chart of The Royal Horticultural Society, London, England, except where general color terms of ordinary dictionary significance are used.

Botanical classification: Dianthus 'Red Dwarf'.
Species: ×hybrida.
Common name: Carnation.
Commercial classification: Herbaceous perennial.
Use: Container and landscape plant.
Parentage: 'Red Dwarf' is a hybrid that resulted from the induced hybridization of the following parent plants:
- *Female parent.*—Dianthus 'Brehemen' (unpatented).
- *Male parent.*—Unidentified Dianthus.

Plant description:
- *Bloom period.*—Can blomm all year, but specific blooming period is April to October.
- *Plant habit.*—Plants form a tight, compact cushion.
- *Plant sexuality.*—Hermaphrodite.
- *Height.*—10–12 cm. in height (including flower stalks).
- *Width.*—20–25 cm. in width.
- *Hardiness.*—Hardy to minus 15° Centigrade.
- *Vigor.*—Vigorous. 250% of the vigour of 'Fusilier'.
- *Type.*—Perennial herb.
- *Root system.*—Fine, fibrous, deep rooting system.
- *Propagation.*—Propagation is accomplished with softwood shoot cuttings.
- *Cultural requirements.*—Plant in full sun and well drained loam or sandy loam of good physical structure with a pH of 6.5–7.0. This variety needs a high light intensity and long days.
- *Diseases and pests.*—Susceptible to known Dianthus pests and disease but no other susceptibilities are known to the inventor.
- *Time required to produce roots.*—2–3 weeks is needed to produce roots on initial cutting.
- *Temperature recommended for cuttings to produce roots.*—The air temperature required is 15–18° Centigrade and the base heat required is 21° Centigrade.
- *Crop time.*—4–7 months in needed for a rooted cutting to reach a finished one-gallon container size.

Stem:
- *Shape.*—Cylindrical.
- *Stem dimensions.*—5 cm. in length and 0.25 cm. in diameter.
- *Stem surface.*—Glabrous and waxy.
- *Stem color.*—122A.
- *Branching.*—Numerous basal breaks.
- *Internode length.*—4–5 cm. between nodes.
- *Node color.*—133B.
- *Node dimensions.*—0.50 cm. in diameter and 0.50 cm. in height.

Foliage:
- *Type.*—Evergreen.
- *Shape.*—Linear.
- *Division.*—Simple.
- *Apex.*—Cuminate.
- *Base.*—Concave.
- *Venation pattern.*—Parallel but not visible to the naked eye.
- *Vein color* (*abaxial surface*).—137A.
- *Vein color* (*adaxial surface*).—133A.
- *Margins.*—Rough and serrate.
- *Attachment.*—Sessile.
- *Stipules.*—None.
- *Petiole.*—None.
- *Arrangement.*—Opposite.
- *Surface* (*adaxial and abaxial*).—Waxy.
- *Leaf dimensions.*—40 mm. in length and 2 mm. in width (3 mm. near the leaf tip).
- *Leaf color* (*adaxial surface*).—133A.
- *Leaf color* (*abaxial surface*).—137A.
- *Fragrance.*—None.

Flowers:
- *Type.*—Solitary or 1–3 per stem.
- *Persistent or self-cleaning.*—Persistent.
- *Flower dimensions.*—25 mm. in height (including the calyx, corolla and petals) and 35 mm. in diameter.
- *Flower shape.*—Disc shaped.
- *Throat depth.*—15 mm. in depth.
- *Aspect.*—Facing upward.
- *Bud dimensions.*—12 mm. in height and 4 mm. in diameter.
- *Bud shape.*—Tubular and pointed.
- *Bud color.*—On the same plant there are buds that are the color 46A and buds that are the color 46B. The tightly closed buds are 46A and the buds that are just beginning to open are 46B.
- *Petals.*—5 in one whorl.
- *Petals fused or unfused.*—Unfused.
- *Petal margin.*—Irregular with 1–4 mm. indentations.
- *Petal shape.*—Fan shaped. 80° segment with strap forming the tube attached below the ovary.
- *Petal color.*—46C with a darker center of 53A.
- *Corolla tube color* (*outside*).—155A.
- *Petal surface.*—Lustrous.
- *Calyx dimensions.*—5 mm. in width and 12 mm. in length.
- *Calyx color.*—135B.
- *Epicalyx.*—5 scales.
- *Epicalyx color.*—135B.
- *Number of sepals.*—5 in number.

*Sepals fused or unfused.*—Fused.
*Sepal shape.*—Tubular.
*Sepal margins.*—Point minutely toothed.
*Sepal apex.*—Acuminate.
*Peduncle dimensions.*—5 cm. in length and 1 mm. in width.
*Peduncle color.*—136B.
*Peduncle surface.*—Waxy.
*Fragrance.*—Moderate clove perfume.
*Lastingness of individual flower.*—10 days.

Reproductive organs:
*Stamens.*—Ten in number.
*Stamen color.*—75C.
*Anther color.*—75C.
*Anther shape.*—Lanceolate.
*Amount of pollen.*—Low.
*Pistil.*—2.
*Pistil color.*—75C.
*Pistil shape.*—Hair-like.
*Stigma.*—Single.
*Stigma color.*—75C.
*Style color.*—75C.
*Stigma dimensions.*—0.5 mm. in width and 5 mm. in length.
*Ovary position.*—Superior.
*Ovary color.*—144B near top and 144C near bottom.
*Ovary shape.*—Oval.
*Ovary dimensions.*—7 mm. in height and 2 mm. in width.

Seed production:
*Seeds.*—Produced if pollinated with another variety, but will not self-pollinate.
*Seed number.*—When seed is produced there are 1–10 seeds produced.
*Seed shape.*—Rounded and flattened.
*Seed surface.*—Crinkled surface.
*Seed color.*—202A.
*Seed dimensions.*—2.5 mm. in diameter and 3 mm. in length.
*Fruit shaped.*—Capsule.
*Fruit size.*—8 mm. in height and 3 mm. in width.
*Fruit color.*—149D.

I claim:

1. A new and distinct cultivar of Dianthus plant named 'Red Dwarf' as described and illustrated herein.

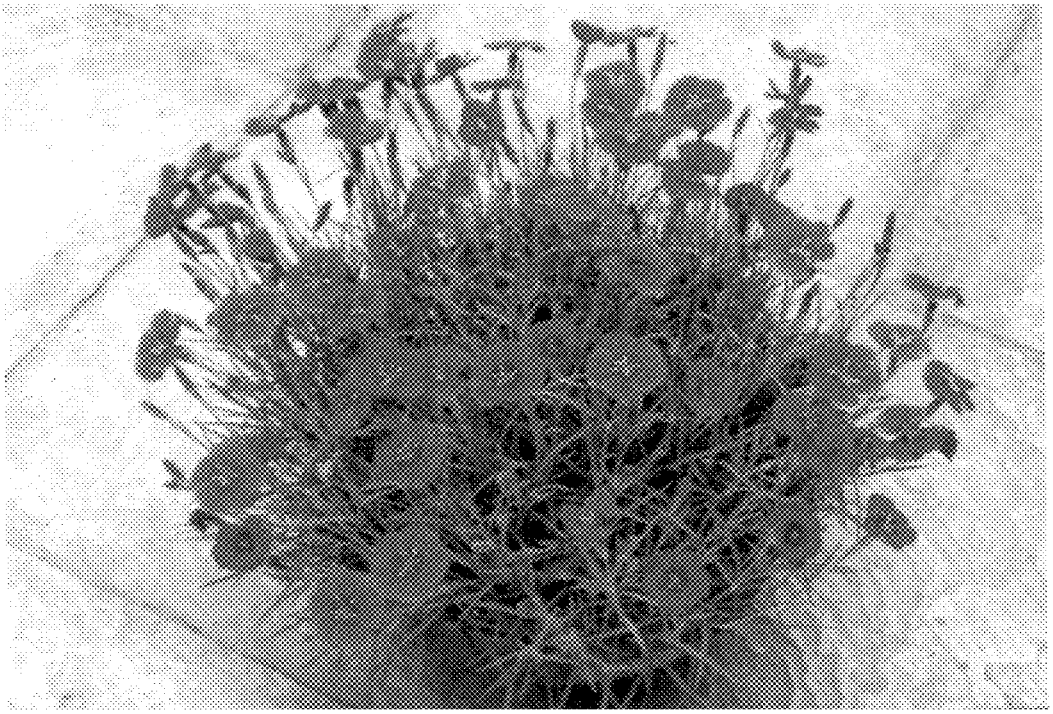

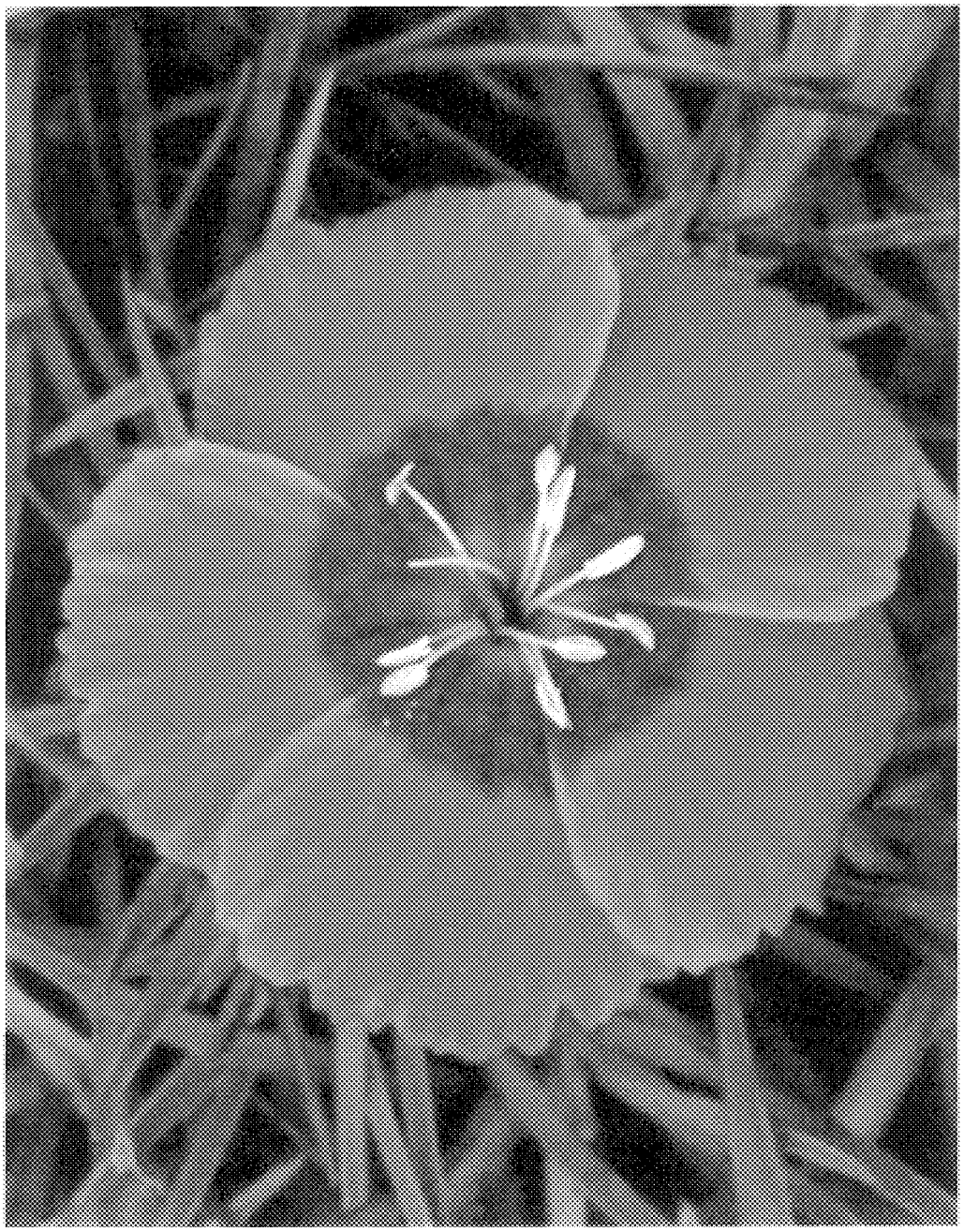

* * * * *